(12) United States Patent
Gebre et al.

(10) Patent No.: US 11,783,165 B1
(45) Date of Patent: Oct. 10, 2023

(54) GENERATING VECTORS FROM DATA

(71) Applicant: KONINKLIJKE PHILIPS N.V., Eindhoven (NL)

(72) Inventors: Binyam Gebrekidan Gebre, Rosmalen (NL); Christine Menking Swisher, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 916 days.

(21) Appl. No.: 16/587,210

(22) Filed: Sep. 30, 2019

Related U.S. Application Data

(60) Provisional application No. 62/740,155, filed on Oct. 2, 2018.

(51) Int. Cl.
*G06N 3/045* (2023.01)
*G06N 3/08* (2023.01)

(52) U.S. Cl.
CPC .................. *G06N 3/045* (2023.01); *G06N 3/08* (2013.01)

(58) Field of Classification Search
CPC ................. G06N 3/0454; G06N 3/08
See application file for complete search history.

(56) References Cited

U.S. PATENT DOCUMENTS

| | | | |
|---|---|---|---|
| 10,565,498 B1* | 2/2020 | Zhiyanov | G06N 7/005 |
| 2017/0076152 A1 | 3/2017 | Asl et al. | |
| 2017/0161455 A1* | 6/2017 | Grady et al. | G16H 30/20 |
| 2017/0161590 A1* | 6/2017 | Boulkenafed et al. | G06K 9/6269 |
| 2017/0357896 A1 | 12/2017 | Tsatsin et al. | |

(Continued)

OTHER PUBLICATIONS

Berlemont, S. et al., "Class-balanced siamese neural networks". Neurocomputing 273 (2018) 47-56.
English-language version of the CN search report citing D1, which was applied as an alleged prior art reference against claims 1-15.
Miotto, R. et al., "Deep patient: an unsupervised representation to predict the future of patients from the electronic health records". Sci Rep. 2016; 6: 26094.
Schroff, F. et al., "FaceNet: A unified embedding for face recognition and clustering". 2015 IEEE Conference on Computer Vision and Pattern Recognition (CVPR); 2015 ():815-823; 10.1109/CVPR.2015.7298682.

(Continued)

*Primary Examiner* — David Bilodeau

(57) ABSTRACT

The invention discloses an apparatus for converting data and for assessing data. The apparatus comprises a processor. For converting data, the processor is configured to train a neural network arrangement to generate a first vector to represent input data, each element of the first vector representing a defined feature of the input data. For assessing data, the processor is configured to provide a neural network trained to generate a first vector representing input data; provide input data to the trained neural network; and generate, using the trained neural network, a first vector representing the input data, wherein each element of the generated first vector represents a defined feature of the input data. Methods and a computer program product are also disclosed.

19 Claims, 5 Drawing Sheets

(56) References Cited

U.S. PATENT DOCUMENTS

| | | | |
|---|---|---|---|
| 2018/0041536 A1* | 2/2018 | Berlin | G06N 3/08 |
| 2018/0107798 A1 | 4/2018 | Hu | |
| 2018/0196873 A1* | 7/2018 | Yerebakan et al. | G06F 16/35 |
| 2018/0218429 A1* | 8/2018 | Guo et al. | G06V 30/194 |
| 2018/0247195 A1 | 8/2018 | Kumar et al. | |

OTHER PUBLICATIONS

Taigman, Y. et al., "Deepface: closing the gap to human-level performance in face verification". IEEE Computer Society. 2014IEEE Conference on Computer Vision and Pattern Recognition.

Wang, J. et al., "A Multi-resolution approach for spinal metastasis detection using deep Siamese neural networks". Computers in Biology and Medicine 84 (2017) 137-146.

Yan, K. et al., "Deep lesion graphs in the wild: relationship learning and organization of significant radiology image findings in a diverse large-scale lesion database". arXiv:1711.10535. Attention drawn to Section 2 "Related Work".

Zhiyin, C.; "Application Research of Image Retrieval Based on Deep Neural Network", Chinese excellent Master s Theses Full text Database (Information and Science Technology), 2018, No. 07, pages 1-73.

\* cited by examiner

GENERATING VECTORS FROM DATA

FIELD OF THE INVENTION

The invention relates to an apparatus for generating vectors from data and, in particular, to generating vectors from input data using a neural network arrangement.

BACKGROUND OF THE INVENTION

In clinical settings, it is useful, and sometimes very important, to be able to compare patient data, such as patient records, in order to identify and measure similarities and differences between them. For example, from a comparison of a medical imaging scan acquired from a patient diagnosed with cancer with a medical imaging scan acquired from a patient suspected of having cancer, it may be possible to identify common or dissimilar features in the two scans and, therefore, it may be possible to provide a diagnosis of the patient suspected of having cancer. However, diversity in data acquisition techniques and data acquisition modalities means that it is not easy to compare data from different patients, particularly if the data is in different formats. Similarly, it is not easy to compare data acquired at different times from the same patient, if the data is in different formats. For example, it is not a straightforward task to compare an x-ray scan acquired from one patient with an MRI scan acquired from another patient. Similarly, it is not a straightforward task to compare a medical imaging scan with a written report, even though the written report may contain much of the information contained within the medical imaging scan. The difficulties discussed above extend in a more general sense to other types of data, beyond the healthcare sector.

Therefore, it would be useful to be able to compare data in a more consistent manner. For example, it would be useful to be able to compare data acquired from different sources (e.g. medical imaging modalities) and to compare data in different formats. It would also be useful to be able to analyze data in a more effective manner than by studying the raw data itself.

SUMMARY OF THE INVENTION

It has been recognized that a more reliable and consistent comparison of data may be made if the data is converted into a common format prior to being assessed or compared. Specifically, a better comparison of data can be made if the data is first converted into vectors. According to embodiments disclosed herein, data (e.g. patient data) may be converted into a vector of a particular length (i.e. having a defined number of elements) using a neural network arrangement.

According to a first aspect, various embodiments disclosed herein provide an apparatus for converting data, the apparatus comprising a processor configured to train a neural network arrangement to generate a first vector to represent input data, each element of the first vector representing a defined feature of the input data.

The neural network arrangement may, in some embodiments, comprise a plurality of identical neural networks. Each neural network of the plurality of identical neural networks may be trained using different training data.

In some embodiments, the neural network arrangement may comprise a Siamese neural network arrangement.

The neural network arrangement may, in some embodiments, comprises three neural networks. The processor may be configured to train the three neural networks using a triplet of input data, a first data element of the triplet of input data comprising a reference data element which falls within a defined class, a second data element of the triplet of input data which falls within the defined class and a third data element of the triplet of input data which does not fall within the defined class.

In some embodiments, a defined feature of the input data for which the neural network arrangement is capable of representing using an element of the first vector may be represented by a non-negative number.

According to a second aspect, various embodiments disclosed herein provide an apparatus for assessing data, the apparatus comprising a processor configured to provide a neural network trained to generate a first vector representing input data; provide input data to the trained neural network; and generate, using the trained neural network, a first vector representing the input data, wherein each element of the generated first vector represents a defined feature of the input data.

The processor may be further configured to identify one or more vectors in a database of vectors which are within a defined threshold similarity distance of the first vector.

In some embodiments, the processor may be configured to determine a similarity distance between at least one element of the first vector and a corresponding at least one element of a second vector. The first vector and the second vector may be (i) vectors representing input data from different patients; or (ii) vectors representing input data from the same patient, the input data acquired at two different times.

The input data may comprise patient medical data.

According to a third aspect, various embodiments disclosed herein provide a method for converting data, the method comprising training a neural network arrangement to generate a first vector to represent input data, each element of the first vector representing a defined feature of the input data.

According to a fourth aspect, various embodiments disclosed herein provide a method for assessing data, the method comprising providing a neural network trained to generate a first vector representing input data; providing input data to the trained neural network; and generating a first vector representing the input data, wherein each element of the generated first vector represents a defined feature of the input data.

In some embodiments, the method may further comprise identifying one or more vectors in a database of vectors which are within a defined threshold similarity distance of the generated first vector.

The method may further comprise determining a similarity distance between at least one element of the first vector and a corresponding at least one element of a second vector.

According to a fifth aspect, various embodiments disclosed herein provide a computer program product comprising a non-transitory machine-readable medium, the machine-readable medium having machine-readable code embodied therein, the machine-readable code being configured such that, on execution by a suitable computer or processor, the computer or processor is caused to perform steps of the methods disclosed herein.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

According to embodiments disclosed herein, a neural network arrangement may be trained to convert input data into a vector. The vector may, for example, comprise a vector having a defined length, such as a defined number of vector elements or components. In some examples, a vector and which data is converted may comprise 128 vector elements. In other examples, more or fewer vector elements may be included in each vector. Each element of the vector represents a defined feature of the input data. In other words, each element of a vector may correspond to or describe a particular feature contained within the data, such that corresponding elements in different vectors relate to the same feature and, therefore, may be compared with one another.

Some aspects of the invention disclosed herein are described in the context of a clinical setting, wherein medical data (e.g. medical data relating to a patient) is used to generate a vector, so that multiple patients can be compared to one another, or so that data acquired from a single patient at different times can be compared. However, it will be apparent that embodiments disclosed herein may be applied in fields other than the medical field. In general, a vector may be generated according to the present invention using any kind of data.

According to a first aspect, embodiments disclosed herein provide an apparatus for converting data and, according to a second aspect, embodiments disclosed herein provide an apparatus for assessing data. The conversion of data and this data may be carried out using the same apparatus as described below.

Figure 1:
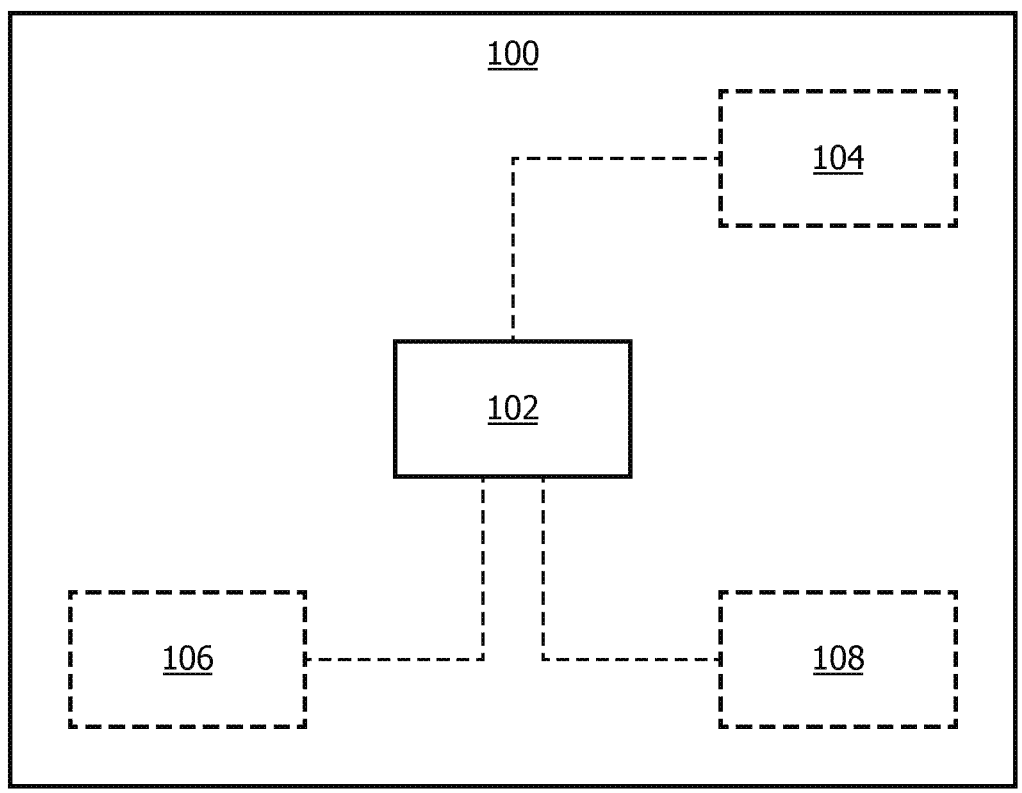
FIG. 1 is a schematic illustration of an example of an apparatus according to various embodiments.

Referring to the drawings, FIG. 1 shows a block diagram of an apparatus 100 that can be used for converting and/or assessing data. With reference to FIG. 1, the apparatus 100 comprises a processor 102 that controls the operation of the apparatus 100 and that can implement the methods described herein. The apparatus 100 may further comprise a memory 106 comprising instruction data representing a set of instructions. The memory 106 may be configured to store the instruction data in the form of program code that can be executed by the processor 102 to perform the methods described herein. In some implementations, the instruction data can comprise a plurality of software and/or hardware modules that are each configured to perform, or are for performing, individual or multiple steps of the method described herein. In some embodiments, the memory 106 may be part of a device that also comprises one or more other components of the apparatus 100 (for example, the processor 102 and/or one or more other components of the apparatus 100). In alternative embodiments, the memory 106 may be part of a separate device to the other components of the apparatus 100. For example, the apparatus 100 may be implemented as part of a cloud computing environment.

The processor 102 of the apparatus 100 can be configured to communicate with the memory 106 to execute the set of instructions. The set of instructions, when executed by the processor 102 may cause the processor to perform steps of the methods described herein. The processor 102 can comprise one or more processors, processing units, multi-core processors or modules that are configured or programmed to control the apparatus 100 in the manner described herein. In some implementations, for example, the processor 102 may comprise a plurality of processors, processing units, multi-core processors and/or modules configured for distributed processing. It will be appreciated by a person skilled in the art that such processors, processing units, multi-core processors and/or modules may be located in different locations and may each perform different steps and/or different parts of a single step of the methods described herein.

In some embodiments, as illustrated in FIG. 1, the apparatus 100 may comprise at least one user interface 104 configured to receive any of the user inputs described herein. The user interface 104 may allow a user of the apparatus 100 to manually enter instructions, data, or information relating to the method described herein. In some embodiments, the user interface 104 may be used to present content to a user. The user interface 104 may be any type of user interface that enables a user of the apparatus 100 to provide a user input (e.g. input data from which a vector is to be generated), interact with and/or control the apparatus 100. For example, the user interface 104 may comprise one or more switches, one or more buttons, a keypad, a keyboard, a mouse, a touch screen, a microphone or an application (for example, on a tablet or smartphone), or any other user interface, or combination of user interfaces that enables the user to provide data to the apparatus and/or via which the user can consume information from the apparatus 100.

In some embodiments, the user interface 104 (or another user interface of the apparatus 100) may enable rendering (or output or display) of information, data or signals to a user of the apparatus 100. As such, a user interface 104 may be for use in providing a user of the apparatus 100 with information relating to or resulting from the method according to embodiments herein. For example, in some embodiments, the user interface 104 may display a generated vector to a user. The processor 102 may be configured to control one or more user interfaces 104 to provide information resulting from the method according to embodiments described herein. For example, the processor 102 may be configured to control one or more user interfaces 104 to render (or output or display) data using the methods described herein and/or any other outputs of the methods described herein. The user interface 104 may, in some embodiments, comprise a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces for providing information relating to, or resulting from the method, to the user. In some embodiments, the user interface 104 may be part of a device that also comprises one or more other components of the apparatus 100 (for example, the processor 102, the memory 106 and/or one or more other components of the apparatus 100). In alternative embodiments, the user interface 104 may be part of a separate device to the other components of the apparatus 100.

In some embodiments, as illustrated in FIG. 1, the apparatus 100 may also comprise a communications interface (or circuitry) 108 for enabling the apparatus 100 to communicate with any interfaces, memories and devices that are internal or external to the apparatus 100. The communications interface 108 may communicate with any interfaces, memories and devices wirelessly or via a wired connection.

It will be appreciated that FIG. 1 shows the components required to illustrate this aspect of the disclosure and, in a practical implementation, the apparatus 100 may comprise other components in addition to those shown. For example, the apparatus 100 may comprise a battery or other power supply for powering the apparatus 100 or means for connecting the apparatus 100 to a mains power supply.

As noted above, the processor 102 is configured to perform steps of the methods described herein. In some embodiments, a memory (e.g. the memory 106) may be configured to store a set of instructions which, when executed by the processor 102 of the apparatus 100, cause the processor 102 to perform steps or functions as discussed below. According to some embodiments, the processor 102 is configured to train a neural network arrangement to generate a first vector to represent input data, each element of the first vector representing a defined feature of the input data.

As will be apparent from the discussions herein, the input data may, in some embodiments, comprise patient medical data.

In some embodiments, the input data may comprise data in the form of text. For example, in a medical setting, a medical report, such as report written by a radiologist, may be provided to the apparatus 100 as the input data. In some examples, tables and/or charts, for example containing both text and numerical data, may be provided as the input data. Such a table may include details for a particular subject or patient, such as age, gender, smoking status (e.g. smoker or non-smoker), medical diagnosis, and one or more measurements taken from a medical imaging scan. In other examples, the input data may comprise one or more images, including diagrams, photographs, illustrations or images acquired using imaging apparatus, such as a medical imaging scans. A medical image may be acquired using any medical imaging modality or technique including, for example, x-ray imaging, magnetic resonance imaging (MRI), ultrasonography or ultrasound, positron emission tomography (PET), computed tomography (CT) and single-photon emission computed tomography (SPECT). Other imaging modalities that are familiar to those skilled in the art may also be used to acquire a medical image. Thus, such input data may contain a significant amount of information which, in its raw form, may be difficult to compare with corresponding data associated with other subjects. Using the apparatus 100, however, it is possible to convert the data into a format that can more easily be compared. Each feature of a subject's input data (e.g. age, gender, smoking status, lesion size, and so on) may be represented by an element of a vector, such that the same feature for another subject may be analyzed or compared by examining the corresponding element of another subject's vector.

The apparatus 100 is capable of being used to train a neural network arrangement to generate vectors from input data provided to the neural network arrangement. Once the neural network arrangement has been trained, a trained neural network can be used to consistently generate a vector representing new input data provided to the apparatus. While, in some embodiments, the neural network arrangement may comprise a single artificial neural network, in other embodiments, the neural network arrangement may comprise a plurality of artificial neural networks.

Artificial neural networks or, simply, neural networks, will be familiar to those skilled in the art, but in brief, a neural network is a type of model that can be used to classify data (for example, classify, or identify the contents of image data). The structure of a neural network is inspired by the human brain. Neural networks are comprised of layers, each layer comprising a plurality of neurons. Each neuron comprises a mathematical operation. In the process of classifying a portion of data, the mathematical operation of each neuron is performed on the portion of data to produce a numerical output, and the outputs of each layer in the neural network are fed into the next layer sequentially. Generally, the mathematical operations associated with each neuron comprise one or more weights that are tuned during the training process (e.g. the values of the weights are updated during the training process to tune the model to produce more accurate classifications).

For example, in a neural network model for classifying the contents of images, each neuron in the neural network may comprise a mathematical operation comprising a weighted linear sum of the pixel (or in three dimensions, voxel) values in the image followed by a non-linear transformation. Examples of non-linear transformations used in neural networks include sigmoid functions, the hyperbolic tangent function and the rectified linear function. The neurons in each layer of the neural network generally comprise a different weighted combination of a single type of transformation (e.g. the same type of transformation, sigmoid etc. but with different weightings). As will be familiar to the skilled person, in some layers, the same weights may be applied by each neuron in the linear sum; this applies, for example, in the case of a convolution layer. The weights associated with each neuron may make certain features more prominent (or conversely less prominent) in the classification process than other features and thus adjusting the weights of neurons in the training process trains the neural network to place increased significance on specific features when classifying an image. Generally, neural networks may have weights associated with neurons and/or weights between neurons (e.g. that modify data values passing between neurons).

As briefly noted above, in some neural networks, such as convolutional neural networks, lower layers such as input or hidden layers in the neural network (i.e. layers towards the beginning of the series of layers in the neural network) are activated by (i.e. their output depends on) small features or patterns in the portion of data being classified, while higher layers (i.e. layers towards the end of the series of layers in the neural network) are activated by increasingly larger features in the portion of data being classified. As an example, where the data comprises an image, lower layers in the neural network are activated by small features (e.g. such as edge patterns in the image), mid-level layers are activated by features in the image, such as, for example, larger shapes and forms, whilst the layers closest to the output (e.g. the upper layers) are activated by entire objects in the image. More generally, different layers of a neural network may act on different portions of the input data.

In general, the weights of the final layers of a neural network model (known as the output layers) are most strongly dependent on the particular classification problem being solved by the neural network. For example, the weights of outer layers may heavily depend on whether the classification problem is a localization problem or a detection problem. The weights of lower layers (e.g. input and/or hidden layers) tend to depend on the contents (e.g. features) of the data being classified and therefore it has been recognized herein that the weights in input and hidden layers of neural networks processing the same type of data may, with enough training, converge towards the same values over time, even if the outer layers of the models are tuned to address different classification problems.

The neural network(s) of the present disclosure are to be trained to generate a vector representing a first piece or set of input data, such that a similar vector will be generated by the neural network(s) for a similar piece or set of input data. In some examples, the entire vectors of similar input data may be similar. In other examples, individual elements of different vectors may be similar if the features that those elements represent are similar. For example, if a particular element of a vector represents a subject's age, then that element of the vector should be the same, or similar, for two subjects of the same age.

The nature of the vector and/or the vector elements that make up the vector may be chosen based on the intended use of the vector and/or the nature of the subject in respect of whom the vector is to be generated. For example, if vectors are to be generated in respect of subjects who have or who are suspected to have lung cancer, then each element of the vector may represent a feature relevant to lung cancer assessment. Elements of such vectors might correspond to nodule sizes, nodule locations, the age of the subject, the gender of the subject and the subject's smoking status. In this way, each vector may relate to a particular purpose, or class. Taking the lung cancer example, each vector may be specific to the lung cancer class (e.g. a subject may be classified as having lung cancer or as not having lung cancer). Thus, the generated vectors and the vector elements that make up vectors are "designed" to serve a particular purpose. Each element of a vector relates to a particular feature in the input data and, therefore, is interpretable. That is to say it is possible to gain an understanding of a particular feature (and of the subject to whom the vector relates) from the number in a vector element.

Figure 2:
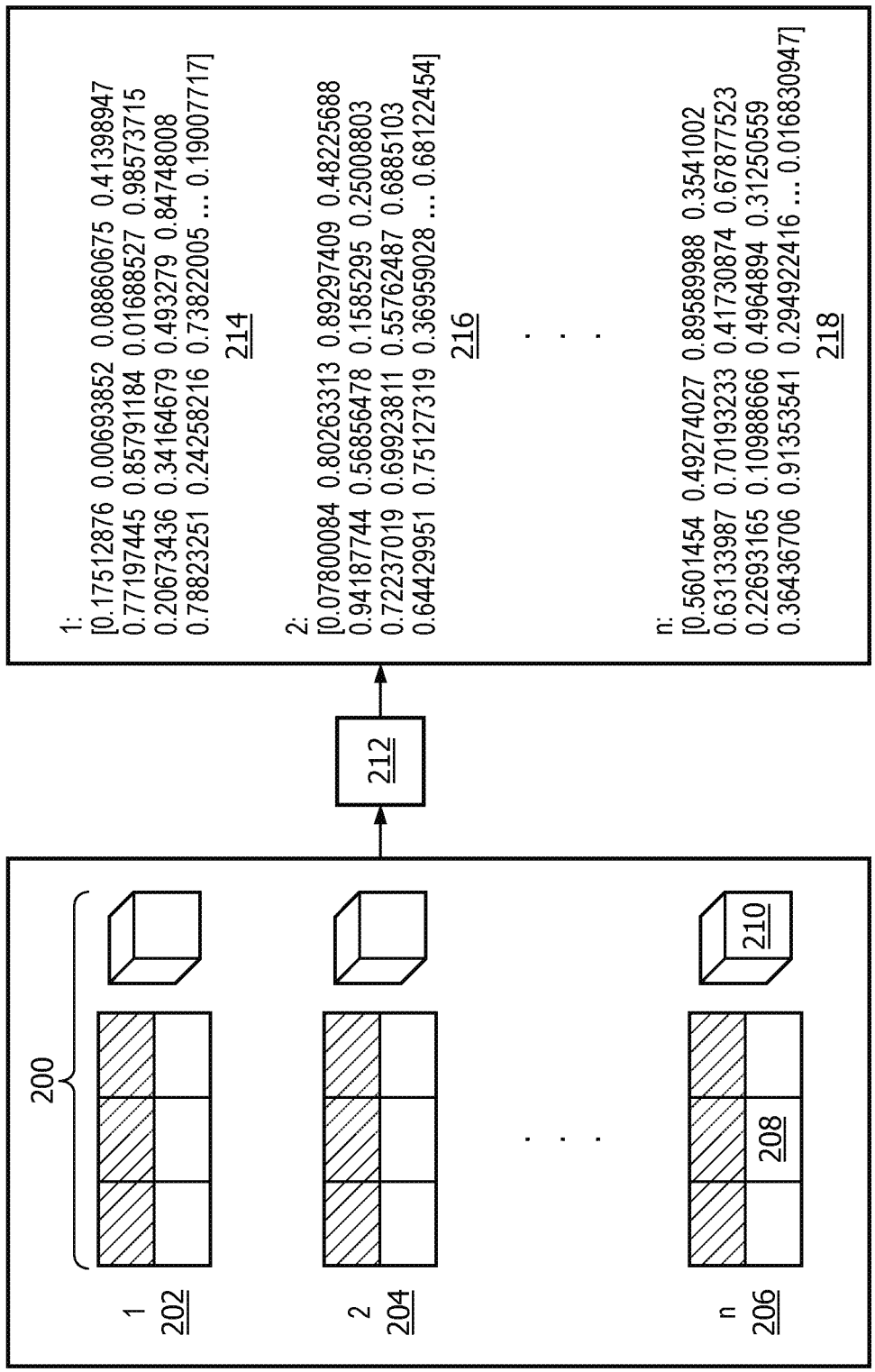
FIG. 2 is an illustration of patient data being converted into vectors.

FIG. 2 is an illustration of an example of data 200 being converted into vectors. In the example shown, data is shown for various subjects 202, 204, 206. For each subject, the input data 200 may be in the form of a table 208 or an image 210. As noted above, input data of other forms may alternatively or additionally be used. The input data is provided to a trained neural network 212, and the neural network generates as its output a vector for each subject. In the example shown, a vector 214 is generated in respect of the first subject 202, the vector 216 is generated in respect of the second subject 204 and a vector 218 is generated in respect of the nth subject 206. Each vector 214, 216, 218 may have a defined length or size which may, for example, be defined by the number of elements included in each vector. In some examples, vector may comprise 128 elements, such that each vector may represent 128 features of the input data. In the example shown in FIG. 2, the first element (or dimension) of the vector 214 is represented by the number 0.17512876, the second element (or dimension) is represented by the number 0.00693852, and so on.

Figure 3:
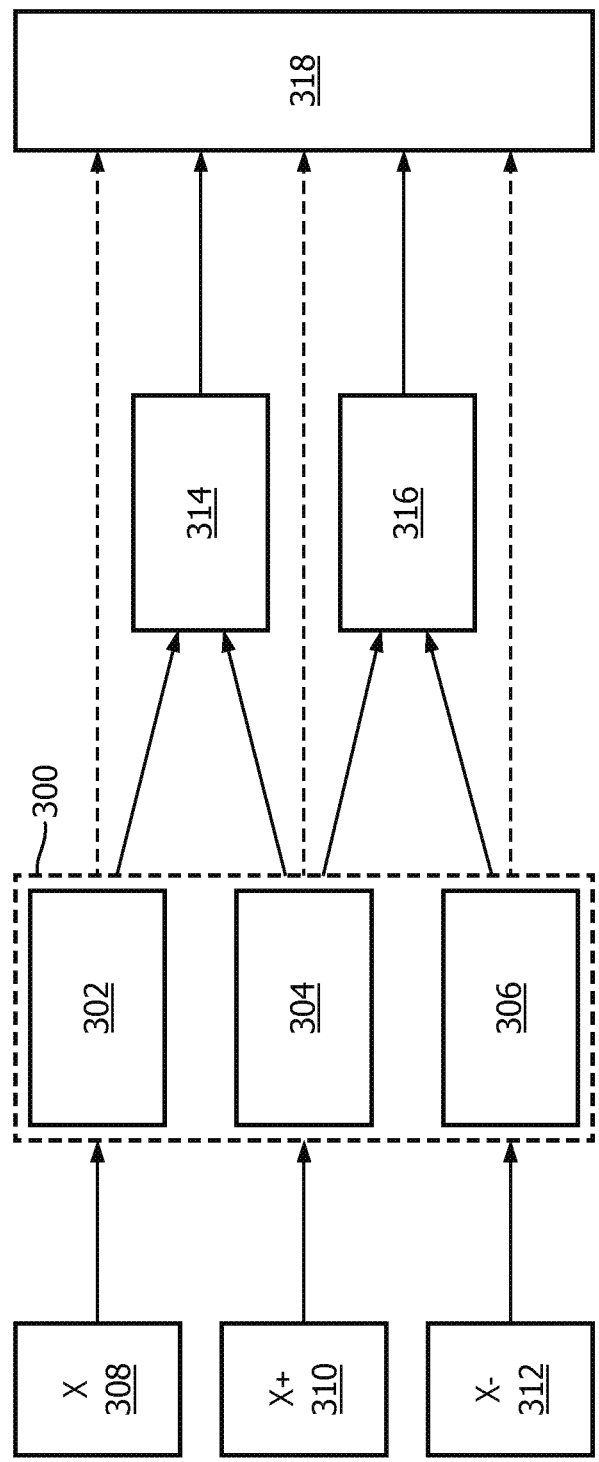
FIG. 3 is schematic illustration of a neural network arrangement according to various embodiments.

In order to obtain a neural network capable of converting input data into a vector which can be reliably used in a comparison with other vectors, it is first necessary to train the neural network to identify the particular features to be represented in the vector, and to generate the numerical vector elements representing those features. FIG. 3 is a schematic illustration of a neural network arrangement that may be used for training purposes in order to obtain a neural network that can generate suitable vectors. FIG. 3 shows a neural network arrangement 300 to be trained in order to obtain a trained neural network for use in generating vectors from input data. In general, the neural network arrangement 300 may comprise a plurality of neural networks. In this example, the neural network arrangement 300 includes a first neural network 302, a second neural network 304, and a third neural network 306. In some embodiments, the neural network arrangement 300 may comprise a plurality of identical neural networks. A first neural network is considered to be identical to a second neural network if the architecture and the weights of the neurons of the first and second neural networks are identical to one another. Each neural network of the plurality of identical neural networks may be trained using different training data. This technique may be used to train the neural networks more efficiently. Such an arrangement, that uses identical neural networks or training, may be referred to as a Siamese neural network arrangement. Thus, the neural network arrangement 300 may, in some embodiments, comprise a Siamese neural network arrangement.

In the example shown in FIG. 3, each of the neural networks 302, 304, 306 is provided with different input data. The first neural network 302 is provided with first input data 308, labelled X in FIG. 3. The first input data 308 may be referred to as a reference data, and this data may relate to, or fall within, a particular class. For example, the first input data 308 may comprise data representative of a first subject who has been diagnosed with lung cancer. The second neural network 304 is provided with second input data 310, labelled X+ in FIG. 3. The second input data 310 may be referred to as matching data, and this data may relate to, or fall within, the same class as the reference data. For example, the second input data 310 may comprise data representative of a second subject who has also been diagnosed with lung cancer. The third neural network 306 is provided with third input data 312, labelled X− in FIG. 3. The third input data 312 may be referred to as non-matching data, and this data may relate to, or fall within, a different class as the reference data and the matching data. In other words, the third input data 312 (i.e. non-matching data) does not relate to, or fall within, the same class as the reference data and the matching data. The three different sets or elements of input data 308, 310, 312 may be referred to as a triplet, and training three separate, but identical, neural networks using such a triplet of data may help the neural networks to train more quickly. Thus, more generally, the neural network arrangement 300 may comprise three neural networks 302, 304, 306. The processor 102 may be configured to train the three neural networks 302, 304, 306 using a triplet of input data, a first data element 308 of the triplet of input data comprising a reference data element which falls within a defined class, a second data element 310 of the triplet of input data which falls within the defined class and a third data element 312 of the triplet of input data which does not fall within the defined class. While a Siamese neural network arrangement may be used in which the neural networks are identical, in some embodiments, non-identical neural networks may also be used within a neural network arrangement, as is discussed in greater detail below.

The aim of the training of the neural networks in the neural network arrangement 300 is to obtain outputs in which a distance between matching pairs of data in the triplet of data (i.e. between X and X+) is relatively small and in which a distance between non-matching pairs of data in the triplet data (i.e. between X and X-) is relatively large. Referring again to FIG. 3, a distance 314 between the vectors generated for the matching (or similar) pair of data (308 and 310) may be determined, and a distance 316 between the vectors generated for the non-matching (or dissimilar) pair of data (310 and 312) may be determined. Distances between vector pairs may be calculated using any suitable technique that will be familiar to those skilled in the art. For example, in one example, a Euclidean distance may be calculated. In other examples, a different technique may be used for determining a distance between the pairs of data, such as determining a Manhattan distance or a cosine distance. While, in some examples, the processor 102 may be used to determine or calculate the distances, in other examples, a separate neural network may be used to calculate the distance. Such a neural network may be designed and trained to calculate a distance between vectors, for example.

In addition to determining distances between vectors representing the matching and non-matching pairs of input data, the processor 102 of the apparatus 100 may be configured to determine a loss 318, to serve as an indicator of the performance of the neural networks in the neural network arrangement. A total loss 318 for a neural network may comprise a combination of a cross entropy loss and a triplet loss (also referred to as a hinge loss). Each neural network in the neural network arrangement 300 is trained (i.e. the weights of the neural network are updated) using backpropagation techniques so as to minimize the total loss. The cross entropy loss may be defined as the negative of the sum of the log of each vector element for which a target is available (i.e. for which a value is available in the data 308, 310, 312). Minimizing the cross entropy loss helps to ensure that individual elements of the vectors correspond to defined features and, therefore, are interpretable. The triplet loss may be defined as follows:

$$\text{triplet loss} = \max\{0, m + d(\text{net}(X), \text{net}(X+)) - d(\text{net}(X), \text{net}(X-))\} \quad [1]$$

where net(X) is a neural network that processes one of the triplets of data (X, X+ or X-); d(net(X), net(X+)) is the distance between matching pairs (i.e. the reference data 308 and the matching data 310); and d(net(X), net(X-)) is the distance between non-matching pairs (i.e. the reference data 308 and the non-matching data 312); and m is a margin (e.g. 0.5 or 1), whereby an aim of the triplet loss function is to make the distance between matching pairs smaller than the distance between non-matching pairs by at least the margin m.

As will be apparent to those skilled in the art, a neural network may be designed to generate an output in any desired form. The embodiments disclosed herein, the output of the neural network(s) comprises a vector having a defined number of vector elements, wherein each element of a vector represents a defined feature of the input data. In some embodiments, a defined feature of the input data for which the neural network arrangement is capable of representing using an element of the first vector is represented by a non-negative number. In other words, the neural network may be designed such that each element of the generated vector is a non-negative number. In some examples, each element of the generated vector may comprise a number between 0 and 1. In such an example, 0 may represent the absence of a particular feature, and 1 may represent the presence of the particular feature. Values between 0 and 1 may be used to represent partial presence, or a degree of severity of a particular feature, for example. Generating a non-negative value for vector elements may be achieved using a sigmoid activation function in the neural network.

Depending on the input data available for training, some features may be evident in some input data but not in others. For example, it may be possible to determine the size of a lesion from input data in the form of an MRI scan, but such information might not be available in input data in the form of a medical report. Thus, if a vector element represents a feature of a particular item input data which cannot be determined, then that element of the vector may be left blank, or may be denoted with some symbol or letter indicating the absence of a value for that particular element. Training of the neural networks in the neural network arrangement 300 may be achieved even if the majority of input training data lacks a particular feature (or information relating to a particular feature). The neural networks may be trained to detect (and determine a vector element value) for a feature if the neural networks are provided with at least a single item of input data which includes information relating to that feature.

Once the neural network arrangement 300 has been trained using the processor 102, a single instance of the neural network (e.g. 302, 304 or 306) may be used to examine or assess input data. For example, a newly-acquired medical imaging scan for any subject may be provided as an input to the trained neural network, and the trained neural network may generate a vector representing the input data. The generated vector can then be used in a comparison with other vectors, so that information on the various features included in the input data can be determined. Thus, with reference again to FIG. 1, according to a second aspect, various embodiments disclosed herein provide an apparatus 100 for assessing data. The apparatus 100 comprises the processor 102. The processor 102 is configured to provide a neural network trained to generate a first vector representing input data. The trained neural network may be the neural network trained using the same apparatus 100, as discussed above. The processor 102 is further configured to provide input data to the trained neural network. The input data may, for example, comprise medical data (e.g. a medical report, a medical image, or a table of information relating to a subject) or any other type of data, as discussed above. The processor 102 is further configured to generate, using the trained neural network, a first vector representing the input data, wherein each element of the generated first vector represents a defined feature of the input data. Thus, the trained neural network generates a vector, which may have a defined number of elements (e.g. 128 elements), and which can subsequently be used for comparison with other vectors generated by the trained neural network. Other vectors generated by the same neural network will relate to the same class, as the neural network will have been trained to look for particular features relevant to that class. For example, when considering data of subjects having or suspected of falling within the class of lung cancer, the neural network is trained to look for features relevant to that disease. Similarly, when the neural network is trained to look for or consider features relevant to other classes (e.g. breast cancer, prostate cancer, diabetes, and the like), then features relevant to the class under consideration will be assessed by the neural network.

The apparatus 100 and/or the processor 102 may use the trained neural network for a number of purposes, as discussed below.

The apparatus 100 may be used to perform a "query-by-example" task. Such a task is used to retrieve data (e.g. medical imaging scans) that match some query data (e.g. a query scan). Such a task can be performed efficiently using vector representations. Thus, the processor 102 may be further configured to identify one or more vectors in a database of vectors which are within a defined threshold similarity distance of the first vector. In other words, a vector generated in respect of an item of input data (e.g. CT scan) may be provided as a query, and the processor 102 may search a memory (e.g. the memory 106) for matching or similar vectors. The memory may contain a database of vectors that have been generated in respect of existing data (e.g. data, such as medical scans, of existing patients). A vector may be considered matching or similar if it falls within a defined threshold similarity distance of the first vector. The distance between the vectors may be determined using the techniques discussed herein. A matching or similar vector to the query vector may correspond to an item of data (e.g. another CT scan) which is similar, or has a large number of similar relevant features to the query data and, therefore, the subject to whom the matching data relates may have medically relevant things in common with the subject to whom the query data relates. Such information may be used for medical assessment, diagnosis, or treatment decisions, for example.

In some embodiments, as described above, the entire vector may be compared with other vectors in order to find matching or similar data in its entirety. However, embodiments disclosed herein also allow an individual element of a vector to be compared with the corresponding element (i.e. the element appearing in the same location in the vector) of other vectors. Thus, the processor 102 may be further configured to determine a similarity distance between at least one element of the first vector and a corresponding at least one element of a second vector. In this way, it is possible to compare a particular feature of query data with the same feature of other data. This provides versatility in that a user may use the apparatus to investigate or assess specific features of data relating to subjects, which may not be apparent from the raw data alone.

As noted above, the apparatus 100 may be used to assess data from multiple subjects, or to assess data from the same subject which, for example, may have been acquired at different times. Thus, the first vector and the second vector may be (i) vectors representing input data from different patients; or (ii) vectors representing input data from the same patient, the input data acquired at two different times. Therefore, the apparatus 100 is able to compare different subjects (and individual features from data of different subjects), and is also able to compare data (e.g. scans) acquired from a single subject over a period of time. In this way, vectors generated from scans acquired, for example, at three-month intervals, can be assessed and compared, so that any changes may be identified. Such techniques may help to predict disease progression, and to monitor changes, such as tumor growth. In some examples, the changes in a vector (or in a vector element) over time may be compared with changes seen in respect of other subjects (e.g. that may be stored in a database), so that unexpected or abnormal changes may be quickly identified. Such insights may provide for more efficient and accurate diagnosis for patients.

The apparatus 100 may be used to perform a "query-by-artificial-example" task. Such a task may be used to test predictions or hypotheses, or to perform research. The task may involve manually creating a vector (e.g. based on previous examples or predictions), and searching a database of existing vectors for matching or similar vectors.

The apparatus 100 may be used to perform a missing attribute/feature value completion task. As noted above, some input data may not explicitly include information relating to all features represented in a vector. Thus, some elements may remain empty, or with a "null" (e.g. non-numerical) entry. If, during training of the neural network, at least one piece of training data is provided containing information for each feature (though no single piece of data needs to include information relating to all features), the trained neural network will look for all of the features. In other words, the trained neural network will attempt to generate a value for all elements of the vector it generates as long as, for each feature it is to consider, it has seen at least one piece of relevant data. In this way, the trained neural network may help to generate values for elements of a vector relating to features which might not previously have been easily identifiable or measurable from the input data.

The apparatus 100 may, in some embodiments, be used for feature extraction tasks. For example, the generated vectors may be used in the automated generation of reports (e.g. radiology reports). In some examples, the generated vectors may be used in a system in order to generate natural language for use in such reports. The use of a vector for such tasks may be more consistent that using the raw input data (e.g. a CT scan) for generating natural language for inclusion in a report.

The apparatus 100 may be used to perform clustering techniques. The interpretable vectors and vector elements may be used for performing cluster analysis for groups of data (e.g. groups of CT scans). By using cluster analysis of the vectors, global properties and hypotheses may be identifiable that may otherwise not have been achievable.

In some embodiments, input data of different formats may be compared using the apparatus 100 and the techniques disclosed herein. For example, the apparatus 100 allows for cross-modality comparisons. That is to say, data of different types, or acquired using different imaging modalities, may be compared to one another. To achieve this, referring again to FIG. 3, the neural network arrangement 300 is trained using input data of different types. For example, the input data X might be a CT scan falling within a particular class (e.g. having features showing evidence of lung cancer), the input data X+ might be a radiology report describing the same CT scan, and the input data X- might be any other report unrelated to the CT scan. The neural network 302 and the neural network 304 are trained to generate similar vectors (i.e. vectors between which there is a low distance) as the inputs of those neural networks both relate to the same subject and class. Thus, the weights and architectures of the neural networks 302 and 304 are not the same as one another as they are looking at different types of input data. However, the weights of the neural network 306 are the same as the weights of the neural network 304 as they are both trained to look for features in the same type of input data (e.g. text-based radiology reports). The trained neural network may therefore be used to generate a vector based on the type of input data used to train it. For example, if the input modality is text (i.e. the input data is a text-based report), then the neural network for text will be used, and the resulting vector can be used for any purpose including for retrieving vectors of medical imaging scans similar to it. This is referred to as cross-modality searching from text to an imaging scan. Similarly, if the provided input modality is an image (e.g. a CT scan), then the neural network for the CT scans will be used and the resulting vector can be used for any purpose including for retrieving vectors of a text-based radiology report similar to it. This is referred to as cross-modality searching from an imaging scan to text.

Figure 4:
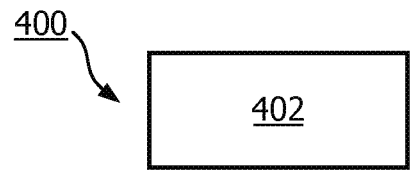
FIG. 4 is a flowchart of an example of a method of converting data according to various embodiments.

According to a third aspect, embodiments disclosed herein provide a method for converting data. FIG. 4 is a flowchart of an example of a method 400 for converting data. The method 400 comprises, at step 402, training a neural network arrangement to generate a first vector to represent input data, each element of the first vector representing a defined feature of the input data.

Figure 5:
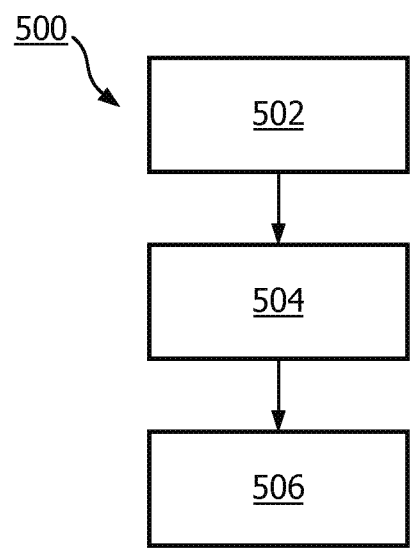
FIG. 5 is a flowchart of an example of a method of assessing data according to various embodiments.

According to a fourth aspect, embodiments disclosed herein provide a method for assessing data. FIG. 5 is a flowchart of an example of a method 500 for assessing data. The method 500 comprises, at step 502, providing a neural network trained to generate a first vector representing input data. At step 504, the method 500 comprises providing input data to the trained neural network. The method 500 comprises, at step 506, generating a first vector representing the input data, wherein each element of the generated first vector represents a defined feature of the input data.

Figure 6:
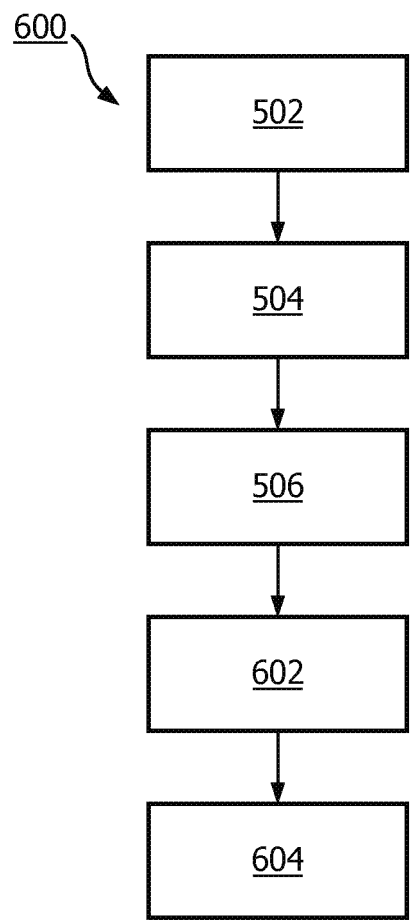
FIG. 6 is a flowchart of a further example of a method of assessing data according to various embodiments.
Figure 7:
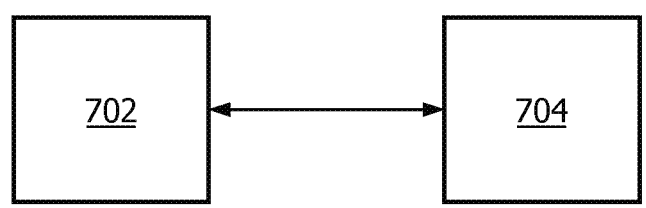
FIG. 7 is a schematic illustration of a processor in communication with a machine-readable medium.

FIG. 6 is a flowchart of a further example of a method 600 for assessing data. The method 600 may comprise steps of the method 500 described above. The method 600 may further comprise, at step 602, identifying one or more vectors in a database of vectors which are within a defined threshold similarity distance of the generated first vector. Thus, similar subjects or cases in a database relating subjects may be identified using the generated vectors.

At step 604, the method 600 may further comprise determining a similarity distance between at least one element of the first vector and a corresponding at least one element of a second vector. Thus, as discussed above, individual elements of vectors may be compared with corresponding elements of other vectors, so that individual feature analysis can be performed.

Steps of the methods 400, 500 may, in some embodiments, be performed using the apparatus 100 described above. Thus, the methods 400, 500 discussed above may comprise one or more additional steps corresponding to the functions of the processor 102 discussed above.

According to a fifth aspect, embodiments disclosed herein provide a computer program product. FIG., 7 is a schematic illustration of an example of a computer program product. The computer program product comprises a non-transitory machine-readable medium 704, the machine-readable medium having machine-readable code embodied therein, the machine-readable code being configured such that, on execution by a suitable computer or processor 702, the computer or processor is caused to perform the steps of the methods 400, 500 disclosed herein.

The processor 102, 702 can comprise one or more processors, processing units, multi-core processors or modules that are configured or programmed to control the apparatus 100 in the manner described herein. In particular implementations, the processor 102, 702 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for converting data, the apparatus comprising:
   a processor configured to:

train a neural network arrangement to generate a first vector to represent the input data, wherein the first vector comprises two or more elements, and wherein each of the two or more elements of the first vector represent a defined feature of the input data, wherein a first element of the first vector exclusively represents one of age, gender, or medical diagnosis exclusively from a first patient, and wherein a different second element of the first vector exclusively represents a different one of age, gender, or medical diagnosis exclusively from the first patient.

2. An apparatus according to claim 1, wherein the neural network arrangement comprises a plurality of identical neural networks; and
wherein each neural network of the plurality of identical neural networks is to be trained using different training data.

3. An apparatus according to claim 1, wherein the neural network arrangement comprises a Siamese neural network arrangement.

4. An apparatus according to claim 1, wherein the neural network arrangement comprises three neural networks; and
wherein the processor is configured to train the three neural networks using a triplet of input data, a first data element of the triplet of input data comprising a reference data element which falls within a defined class, a second data element of the triplet of input data which falls within the defined class and a third data element of the triplet of input data which does not fall within the defined class.

5. An apparatus according to claim 1, wherein a defined feature of the input data for which the neural network arrangement is capable of representing using an element of the two or more elements of the first vector is represented by a non-negative number.

6. An apparatus for assessing data, the apparatus comprising:
a processor configured to:
provide a neural network trained to generate a first vector representing input data;
provide input data to the trained neural network; and
generate, using the trained neural network, the first vector representing the input data, wherein the first vector comprises two or more elements, and wherein each of the two or more elements of the generated first vector represent a defined feature of the input data, wherein a first element of the first vector exclusively represents one of age, gender, or medical diagnosis exclusively from a first patient, and wherein a different second element of the first vector exclusively represents a different one of age, gender, or medical diagnosis exclusively from the first patient.

7. An apparatus according to claim 6, wherein the processor is further configured to:
identify one or more vectors in a database of vectors which are within a defined threshold similarity distance of the first vector.

8. An apparatus according to claim 6, wherein the processor is configured to:
determine a similarity distance between at least one element of the two or more elements of the first vector and a corresponding at least one element of two or more elements of a second vector.

9. An apparatus according to claim 8 wherein the first vector and the second vector are:
(i) vectors representing input data from different patients; or
(ii) vectors representing input data from the same patient, the input data acquired at two different times.

10. An apparatus according to claim 1, wherein the input data comprises patient medical data.

11. A method for converting data, the method comprising:
training a neural network arrangement to generate a first vector to represent input data, wherein the first vector comprises two or more elements, and wherein each of the two or more elements of the first vector represent a defined feature of the input data, wherein a first element of the first vector exclusively represents one of age, gender, or medical diagnosis exclusively from a first patient, and wherein a different second element of the first vector exclusively represents a different one of age, gender, or medical diagnosis exclusively from the first patient.

12. A method for assessing data, the method comprising:
providing a neural network trained to generate a first vector representing input data;
providing input data to the trained neural network; and
generating a first vector representing the input data, wherein the first vector comprises two or more elements, and wherein each of the two or more elements of the generated first vector represents a defined feature of the input data, wherein a first element of the first vector exclusively represents one of age, gender, or medical diagnosis exclusively from a first patient, and wherein a different second element of the first vector exclusively represents a different one of age, gender, or medical diagnosis exclusively from the first patient.

13. A method according to claim 12, further comprising:
identifying one or more vectors in a database of vectors which are within a defined threshold similarity distance of the generated first vector.

14. A method according to claim 12, further comprising:
determining a similarity distance between at least one element of the two or more elements of the first vector and a corresponding at least one element of two or more elements of a second vector.

15. A computer program product comprising a non-transitory machine-readable medium, the machine-readable medium having machine-readable code embodied therein, the machine-readable code being configured such that, on execution by a suitable computer or processor, the computer or processor is caused to perform the method of claim 11.

16. An apparatus according to claim 1, wherein a second vector comprises a primary element and a different secondary element, wherein the primary element exclusively represents one of age, gender, or medical diagnosis exclusively from a different second patient, and wherein the different secondary element exclusively represents a different one of age, gender, or medical diagnosis exclusively from the different second patient.

17. An apparatus according to claim 1, wherein a second vector comprises a primary element and a different secondary element, wherein the primary element exclusively represents one of age, gender, or medical diagnosis exclusively from the first patient at a different time, and wherein the different secondary element exclusively represents a different one of age, gender, or medical diagnosis exclusively from the first patient at the different time.

18. An apparatus according to claim 6, wherein the processor is further configured to:
identify one or more vectors in a database of vectors which are within a defined threshold similarity distance of the first vector; and
determine a similarity distance between at least one element of the two or more elements of the first vector and a corresponding at least one element of two or more elements of a second vector, wherein the second vector comprises a primary element and a different secondary element, wherein the primary element exclusively represents one of age, gender, or medical diagnosis exclusively from a different second patient, and wherein the different secondary element exclusively represents a different one of age, gender, or medical diagnosis exclusively from the different second patient.

19. An apparatus according to claim 6, wherein the processor is further configured to:

identify one or more vectors in a database of vectors which are within a defined threshold similarity distance of the first vector; and determine a similarity distance between at least one element of the two or more elements of the first vector and a corresponding at least one element of two or more elements of a second vector, wherein the second vector comprises a primary element and a different secondary element, wherein the primary element exclusively represents one of age, gender, or medical diagnosis exclusively from the first patient at a different time, and wherein the different secondary element exclusively represents a different one of age, gender, or medical diagnosis exclusively from the first patient at the different time.

* * * * *